United States Patent
DeFreez et al.

(10) Patent No.: US 8,284,398 B2
(45) Date of Patent: Oct. 9, 2012

(54) NEPHELOMETER WITH CONCENTRATION-MODULATED SAMPLE FLOW

(75) Inventors: Richard K. DeFreez, Azalea, OR (US); Michael A. Potter, Wilderville, OR (US); Thomas L. Pottberg, Grants Pass, OR (US)

(73) Assignee: Met One Instruments, Inc., Grants Pass, OR (US)

( * ) Notice: Subject to any disclaimer, the term of this patent is extended or adjusted under 35 U.S.C. 154(b) by 317 days.

(21) Appl. No.: 12/822,497

(22) Filed: Jun. 24, 2010

(65) Prior Publication Data

US 2011/0317162 A1     Dec. 29, 2011

(51) Int. Cl.
*G01J 3/46* (2006.01)
(52) U.S. Cl. ...................................... 356/338
(58) Field of Classification Search .................. None
See application file for complete search history.

(56) References Cited

U.S. PATENT DOCUMENTS

| | | |
|---|---|---|
| 4,380,392 A | 4/1983 | Karabegov et al. |
| 4,408,880 A | 10/1983 | Tsuji et al. |
| 4,613,938 A | 9/1986 | Hansen et al. |
| 5,231,378 A | 7/1993 | Dennis et al. |
| 5,365,559 A | 11/1994 | Hsueh et al. |
| 5,416,581 A | 5/1995 | Kanngiesser |
| 5,502,561 A | 3/1996 | Hutchins et al. |
| 5,684,585 A | 11/1997 | Girvin |
| 5,818,583 A | 10/1998 | Sevick-Muraca et al. |
| 6,208,815 B1 | 3/2001 | Seidel et al. |
| 6,567,165 B1 | 5/2003 | Tsuchiya et al. |
| 7,127,356 B2 | 10/2006 | Nicoli et al. |
| 7,268,873 B2 | 9/2007 | Sevick-Muraca et al. |
| 7,505,132 B2 | 3/2009 | Palumbo |
| 7,551,277 B2 | 6/2009 | Cole |
| 7,600,441 B2 | 10/2009 | Zeng |
| 7,626,698 B2 | 12/2009 | Moriya |
| 2010/0006760 A1* | 1/2010 | Lee et al. .................. 250/338.5 |
| 2010/0039645 A1 | 2/2010 | Ajay |
| 2011/0174078 A1* | 7/2011 | Chinn et al. ..................... 73/657 |

* cited by examiner

*Primary Examiner* — Tu Nguyen
(74) *Attorney, Agent, or Firm* — Schneck & Schneck; Thomas Schneck

(57) ABSTRACT

A nephelometer for detecting the concentration of particulates in a sample aerosol is provided with a branched flow path with a sample aerosol input, a clean gas input and an output leading to an optical sensor unit. At least one of the inputs has periodic variable flow so that a concentration-modulated gas stream is supplied to the optical sensor unit. The detector output of the sensor unit is processed in synchrony with the concentration modulation to filter out DC components, such as 1/f noise and parasitic instrument noise.

16 Claims, 1 Drawing Sheet

NEPHELOMETER WITH CONCENTRATION-MODULATED SAMPLE FLOW

TECHNICAL FIELD

The present invention relates to optical measuring and testing of aerosol samples by particle light scattering, as in a nephelometer instrument, and in particular to reducing DC and parasitic instrument background noise or otherwise separating such noise from the particle scatter signal.

BACKGROUND ART

Nephelometer instruments for measuring the mass per unit volume of ambient aerosols have historically used a light source, such as a diode laser or light-emitting diode (LED), to illuminate a view volume containing particles suspended in a gas carrier. The amount of detected optical scatter from the illuminated particles in the view volume has then been taken as a measure indicative of the amount (mass) of particulate material in the aerosol. Continuous or near-continuous, near-real-time monitoring of the mass, for example in ambient air, can be accomplished by continuously or near-continuously sampling the ambient by pulling the particle carrier gas into and through the instrument view volume. The level of the detected optical signal is then at any time an instantaneous indicator of the mass of particles in the view volume.

Electronic signals suffer from what is known as "1/f noise", contributed for example by the detector. Electronic noise, including the 1/f noise, can be removed or filtered by a technique involving modulation of the light source intensity in time. The amount of light scattered by the illuminated particles in the view volume will thus also be modulated away from a near-DC level. Synchronous detection of the modulated scattering is a sensitive method of separating the modulated scattering signal from the essentially steady level of electronic noise.

Unfortunately, the same detected optical signal also includes a background parasitic scattering from the nephelometer itself, such as scattering from internal optical components or from contaminants within the sensor instruments. Because this parasitic scattering will also be modulated in the same manner as that of the particle scattering, it cannot be separated out by the light modulation technique and forms a background noise level in the instrument underlying the desired particle scatter signal.

What is needed is a nephelometer instrument and noise filtering technique that can not only remove the 1/f or electronic noise, but also the background parasitic scattering contributions of the instrument, so as to obtain a scattering signal that is a more accurate indicator of ambient particle concentration.

SUMMARY DISCLOSURE

The invention is a nephelometer that provides a way to modulate the proportion of ambient sample gas and thus modulate the concentration of particulates that can enter the view volume. Such modulation can be achieved by periodically injecting clean filtered air into the stream of the particle aerosol sample, thereby diluting the particle concentration. Scattering from the particles is modulated synchronously with the proportion of ambient sample gas, while the parasitic instrument scattering is not. The detected scatter signal can then be readily filtered, e.g., with a lock-in amplifier using the sample modulation rate as a reference frequency, so as to separate the synchronously modulated particle signal from the various near-DC or asynchronous contributions of background noise.

The optical source in this nephelometer can operate at a constant output level, i.e. with no modulation. Alternatively, the optical source could still be intensity modulated, e.g. to stabilize the light output against optical-feedback-induced laser noise, but with a modulation frequency much higher than the modulation of the particle concentration. As long as the different forms of modulation have highly disparate and incommensurate frequencies, all of the different noise contributions can be filtered by the synchronous detection technique. A higher signal-to-noise ratio and higher instrument sensitivity results.

DETAILED DESCRIPTION

Figure 1:
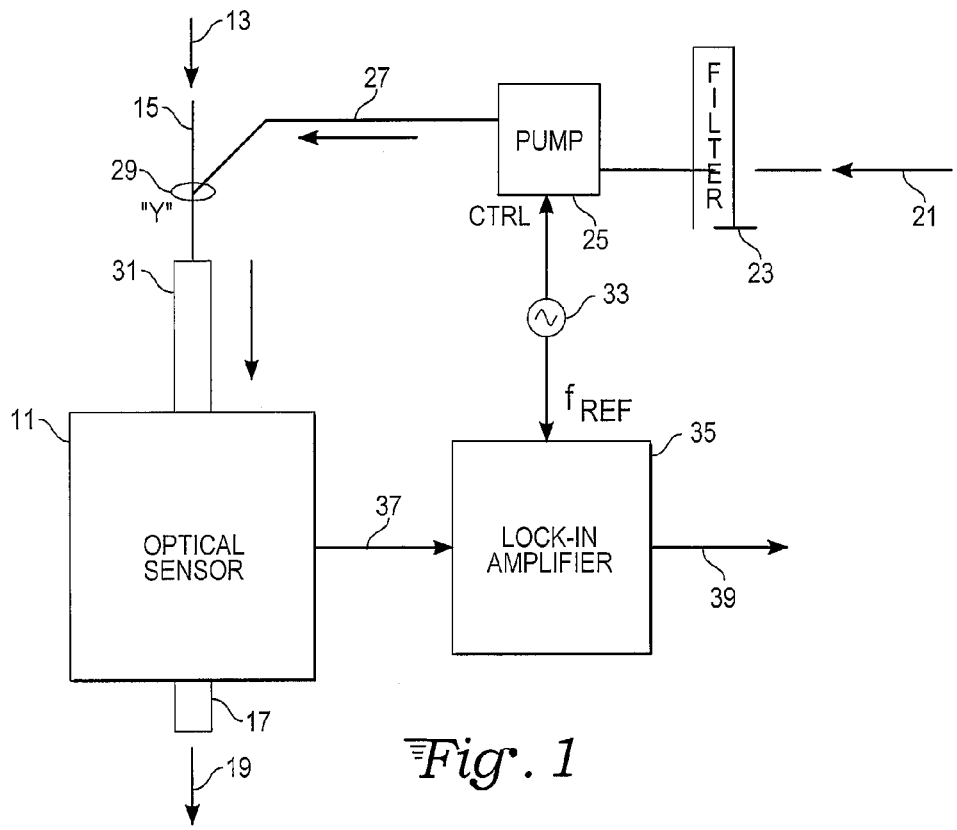
FIG. 1 is a schematic diagram of a first concentration-modulation embodiment of a nephelometer in accord with the present invention.

With reference to FIG. 1, a nephelometer instrument in accord with the present invention includes an optical sensor unit 11, which may be any of the known particle scattering sensors for such instruments, including a light source, such as a diode laser or light-emitting diode (LED), to illuminate a view volume receiving an aerosol sample having particles suspended in a gas carrier, and a light detector positioned to detect light scattered from the illuminated particles in the view volume. The aerosol or particle-laden gas 13 is received through a sample intake 15, flows through the view volume of the optical sensor unit 11, and is then exhausted 19 from the sensor unit's output 17. The particles in the aerosol sample may be solid or liquid and scatter the illuminating light. As in the prior instruments, the light source may provide either constant light output or be intensity modulated at some specified modulation frequency. Intensity modulation of the illumination would generally only be needed where optical-feedback-induced noise of the laser source is expected to be a significant problem. In such cases, the optical modulation frequency should be high enough to stabilize the average intensity against the noise.

The nephelometer instrument also comprises a sample concentration modulation mechanism. In the embodiment of FIG. 1, this mechanism includes a HEPA filter 23 for cleaning an intake gas 21, a non-steady-state pump 25, such as a diaphragm pump, and flow path 27 for the clean air leading into a Y or T junction 29 coupled to the sample intake 15. The relative positions of the filter 23 and pump 25 in the gas flow path can be reversed, particularly if the chosen variable pump 25 is likely to create particles of its own.

In the absence of such a mechanism, a steady or near-steady flow of sample would be pulled through the view volume. However, when activated, the pump 25 periodically introduces pulses of clean air or other gas through one branch of the junction 29 into the flow, thereby periodically diluting the sample. As a result, the input 31 to the optical sensor unit 11 downstream of the junction 29 contains a concentration-modulated aerosol stream as the relative proportions of sample and clean air vary.

Figure 2:
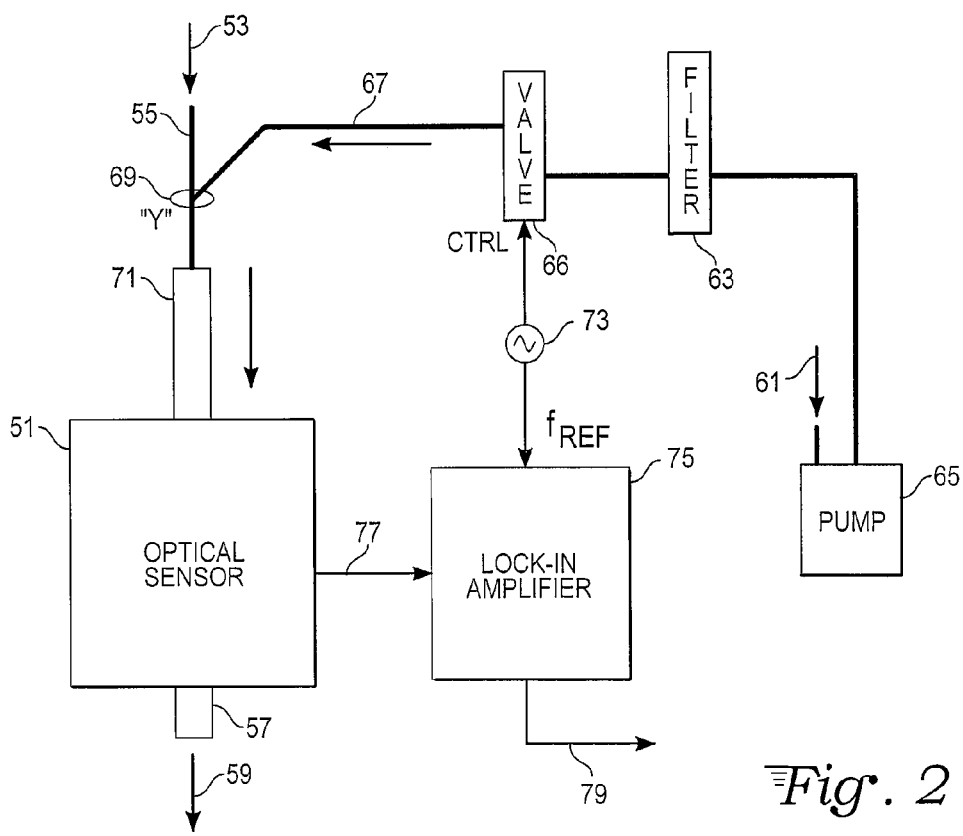
FIG. 2 is a schematic diagram of a second concentration-modulation embodiment of a nephelometer in accord with the present invention.

In alternative embodiments, seen in FIG. 2, the nephelometer instrument again includes an optical sensor unit 51 into the view volume of which is received an aerosol, or particle-laden gas 53 through a sample intake 55. The aerosol sample is thereafter exhausted 59 from the sensor unit's output 57. This instrument likewise includes a sample concentration modulation mechanism, which in this case comprises a steady-state pump 65, such as a rotary vane pump, with a gas intake 61, a HEPA filter 63, and a variable flow valve 66, all leading to a Y or T junction 69 coupled to the sample intake 53. Again, the relative positions of the filter 63, pump 65, and valve 66 can be varied as needed to ensure that gas or air in the flow path 67 is clean. When activated, the pump 65 periodically introduces pulses of clean air or other gas through one branch of the junction 69 into the flow, thereby periodically diluting the sample. As a result, the input 71 to the optical sensor unit 51 downstream of the junction 69 contains a concentration-modulated aerosol stream as the relative proportions of sample and clean air vary. While the supply of clean gas is shown here in a preferred embodiment as being varied using the pump 25 or valve 66, the flow of particle-laden sample aerosol 13 might be varied in addition to or instead of the flow of clean gas.

In either embodiment, the concentration modulation may have an amplitude that swings from all sample to all clean gas (unity modulation depth), or can have lesser modulation depths (non-unity modulation depth) where the concentration varies from all sample to a mixture of sample and clean gas, or from all clean gas to a mixture of sample and clean gas, or from different mixture proportions of sample and clean gas. The non-unity modulation depths would have a reduced signal-to-noise benefit compared to the unity modulation case, so unity modulation depth is preferred.

The detector output 37 or 77 from the optical sensor 11 or 51, representing the detected particle scattering plus noise, is processed in a manner essentially similar to the case of modulated light intensity in order to separate the signal from the noise. In particular, with modulated sample concentration, the particle scattering will modulate according to the relative proportion of sample air. Accordingly, the scattering contribution from the sample can be computed. In particular, the signal processing carried out by the electronics associated with the optical sensor unit 11 or 51 may employ a lock-in amplifier 35 or 75 wherein the detector output 37 or 77 in the sensor unit is mixed with a reference frequency $f_{REF}$ (from oscillator 33 or 73) which is chosen to be the same frequency as the sample concentration modulation rate. Any contribution to the detection signal that is not at the same frequency as the reference frequency will be attenuated essentially to zero by the lock-in amplifier's low pass filter. While any sample modulation profile provided by the diaphragm pump 25 or variable flow valve 66 could be used, the sample modulation will ideally approach a single frequency sinusoidal profile so that signal and noise are separated sufficiently in the frequency domain. As a lock-in amplifier is phase sensitive, the reference frequency $f_{REF}$ may also serve as a variable flow control CTRL for the variable pump 25 or variable flow valve 66, thereby ensuring that the noise filtering by the lock-in amplifier is synchronized with the concentration modulation. The now-filtered detection signal 39 or 79 is output from the lock-in amplifier and may be further processed as in other known nephelometer instruments to obtain particle data for the aerosol sample.

A nephelometer in accord with the invention will provide effective filtering of both 1/f noise and intrinsic instrumental scattering and give a more accurate and more sensitive particle-sensing instrument.

What is claimed is:

1. A nephelometer, comprising:

an optical sensor unit having a light source and a detector positioned to detect light scattered from a view volume;

a flow path coupled to an inlet of the optical sensor, the flow path having a junction with a first inlet branch coupled to receive an aerosol sample and a second inlet branch coupled to receive a supply of a clean gas, at least one of the inlet branches coupled to a pump and adapted to periodically supply the aerosol sample or clean gas in that branch at a specified modulation rate, an outlet of the junction providing a concentration-modulated stream that is variable blend of the aerosol sample and clean gas to the view volume of the optical sensor; and the optical sensor unit further having a signal processor adapted, synchronous with the modulation rate for the concentration-modulated stream, to filter a signal from the detector to remove a background parasitic instrument scattering level and obtain a modulation amplitude of the signal representing a particulate volume in the aerosol sample.

2. A nephelometer as in claim 1, wherein a variable pump modulates the periodic supply.

3. A nephelometer as in claim 1, wherein a variable flow valve modulates the periodic supply.

4. A nephelometer as in claim 1, wherein the second inlet branch periodically supplies clean gas.

5. A nephelometer as in claim 1, wherein a HEPA filter is provided in the flow path for the clean gas.

6. A nephelometer as in claim 1, wherein the signal processor associated with the optical sensor unit includes a lock-in amplifier coupled to receive an output of the detector, the lock-in amplifier mixing the detector output with a reference signal of the same frequency as the modulation rate of the concentration-modulated stream.

7. A nephelometer as in claim 6, wherein the reference signal also serves as a variable flow control for the periodic supply.

8. A nephelometer as in claim 1, wherein the concentration-modulated stream varies between all aerosol sample to all clean gas.

9. A nephelometer as in claim 1, wherein the concentration-modulated stream varies between a mixture of more aerosol sample than clean gas to another mixture of more clean gas than aerosol sample.

10. A method of operating a nephelometer for particle detection in an aerosol sample, the method comprising:

providing a concentration-modulated stream that is a variable blend of a first stream of the aerosol sample and a second stream of clean gas, the flow of at least one of the first and second streams varying periodically at a specified modulation rate;

directing the flow of the concentration-modulated stream into a view volume of an optical sensor unit having a light source and a detector positioned to detect light scattered from the view volume; and processing a detector output from the optical sensor unit to filter the detector output, synchronous with the modulation rate for the concentration-modulated stream, so as to remove a background parasitic instrument scattering level and obtain a modulation amplitude of the signal representing a particulate volume in the aerosol sample.

11. A method as in claim 10, wherein providing a concentration-modulated stream includes modulating a periodic supply of at least one of the aerosol sample and clean gas by means of a variable pump.

12. A method as in claim 10, wherein providing a concentration-modulated stream includes modulating a periodic supply of at least one of the aerosol sample and clean gas by means of a variable flow valve.

13. A method as in claim 10, wherein the concentration-modulated stream varies between all aerosol sample and all clean gas.

14. A method as in claim 10, wherein the concentration-modulated stream varies between a mixture of more aerosol sample than clean gas to another mixture of more clean gas than aerosol sample.

15. A method as in claim 10, wherein processing the detector output from the optical sensor unit includes supplying the detector output to a lock-in amplifier mixing a reference signal with a frequency synchronized to the concentration modulation.

16. A method as in claim 15, wherein the reference signal doubles as a control for the flow of the at least one periodically varying stream.

* * * * *